United States Patent [19]

Skibida et al.

[11] Patent Number: 5,495,034
[45] Date of Patent: Feb. 27, 1996

[54] METHOD FOR PREPARING α-SUBSTITUTED ω-HYDROPERFLUOROALKANES

[75] Inventors: Irina P. Skibida; Andrei M. Sakharov, both of Moscow; Jury L. Bakhmutov; Vladimir F. Denisenkow, Perm; Nina P. Martynova, Perm, all of Russian Federation

[73] Assignee: Hoechst Aktiensellschaft, Germany

[21] Appl. No.: 244,881

[22] PCT Filed: Dec. 19, 1991

[86] PCT No.: PCT/SU91/00266

§ 371 Date: Jul. 15, 1994

§ 102(e) Date: Jul. 15, 1994

[87] PCT Pub. No.: WO93/12059

PCT Pub. Date: Jun. 24, 1993

[51] Int. Cl.⁶ .................................................. C07C 51/16
[52] U.S. Cl. .......................... 554/135; 554/226; 554/132; 570/123; 570/124; 570/261
[58] Field of Search ................................. 554/135, 226; 570/261, 123, 124

[56] References Cited

U.S. PATENT DOCUMENTS

| | | | |
|---|---|---|---|
| 2,115,892 | 5/1938 | Toussaint | 260/116 |
| 3,525,758 | 8/1970 | Katsushima et al. | 260/408 |
| 3,799,995 | 3/1974 | Hutchinson | 260/653 |
| 4,348,509 | 9/1982 | Sanders et al. | 562/538 |
| 4,546,203 | 10/1985 | Metzner | 562/538 |
| 4,879,068 | 11/1989 | Chiarino et al. | 260/397 |
| 4,976,893 | 12/1990 | Leupold | 260/413 |

*Primary Examiner*—José G. Dees
*Assistant Examiner*—Deborah D. Carr
*Attorney, Agent, or Firm*—Curtis, Morris & Safford

[57] ABSTRACT

A method for the preparation of α-substituted ω-dihydroperfluoroalkane derivatives of the general formula $H(CF_2CF_2)_nR$ wherein R=H or COOH, and n=1–10 is characterized by oxidizing α, α, ω-trihydroperfluoroalcohols with an oxygen gas or an oxygen-containing gas in the presence of a homogeneous copper catalyst and an alkaline agent in an organic solvent with subsequent isolation of the desired product.

6 Claims, No Drawings

METHOD FOR PREPARING α-SUBSTITUTED ω-HYDROPERFLUOROALKANES

This application is 371 of PCT/5091/0026 filed Dec. 19, 1991.

FIELD OF THE INVENTION

The present invention is in the field of organic chemistry. More particularly, the invention relates to a method for preparing α-substituted ω-hydroperfluoroalkanes.

BACKGROUND OF THE INVENTION

Known in the art are methods to prepare α-substituted ω-hydroperfluoroalkanes, for example, a method for the preparation of dihydroperfluoroalkanes which includes photoinitiated chlorination of α, α, ω-trihydroperfluoroalcohols (telomeric alcohols) of the general formula: $H(CF_2CF_2)_nCH_2OH$ wherein n=1–5 (Brace Neal. O, J. Org. Chem., 1961, 26, No. 10, pp. 4005–4010). The reaction process proceeds at a temperature of 10° to 30° C. for 2–7 hours to form the corresponding aldehydes that are then converted into dihydroperfluoroalkanes by treatment of them with 50% aqueous solution of potassium hydroxide.

This method has proved, however, faulty for its complicated production process associated with the employment of UV light sources and an aggressive and toxic chlorine medium, and the necessity of conducting the process in two stages. The method has a low conversion (10–25%) of the starting materials and a sufficiently low selectivity of the reaction yield (38–68%) of the desired products in terms of the amount of the converted alcohol (yields of the desired products are less than 17% based on alcohol to be charged). It should be also noted that the formation of aldehydes is accompanied by evolution of HCL gas, and, therefor, further neutralization step should be added. For the reasons as stated above this method failed to find industrial use.

Known in the art are the processes to prepare ω-hydroperfluorocarboxylic acids, which include the oxidation reaction of α, α, ω-trihydroperfluoroalcohols (telomeric alcohols) with various oxidizing agents.

It has been proposed a method for the preparation of ω-hydroperfluorocarboxylic acids of the formula $H(CF_2CF_2)_nCOOH$ wherein n=1–4, which includes the oxidation reaction of telomeric alcohols with nitric oxides (see, SU, A, No. 314748). The oxidation reaction is carried out at a temperature of 350° to 400° C. with 4 moles of nitrogen dioxide used for 1 mol of the initial alcohol. The yields of ω-hydroperfluorocarboxylic acids having odd number of carbon atoms are 43.4% for ω-hydroperfluorovaleric acid and 48.0% for ω-hydroperfluoroenanthic acid. Thus, this method does not ensure high yields of the desired products. In addition, the oxidation reaction is carried out at high temperatures, and the treatment of the resulting aggressive mixture consisting of ω-hydroperluorocarboxylic acids, nitric oxides, hydrofluoric acid and nitrogen-containing acids requires special corrosion-resistant equipment.

Further, there is proposed a method for the preparation of ω-hydroperfluorocarboxylic acids of the general formula $H(CF_2CF_2)_nCOOH$ wherein n=3–6, which includes oxidizing telomeric alcohols with potassium permanganate in glacial acetic acid at a temperature of 50° to 105° C. (see, U.S. Pat. No. 3,423,417; U.S. Pat. No. 3,514,322 and U.S. Pat. No. 2,559,629). In order to recover the desired products, the reaction mixture, according to the invention, is filtered to remove manganese dioxide, and alternatively, treated with sulfur dioxide to convert $MnO_2$ into manganese sulfate. Then, glacial acetic acid is removed by evaporation, the residue is acidified with sulfuric acid and extracted with ether. The ether extract is distilled off, and the acids is treated by recrystallization.

This method is faulty for its complicated production process and a large quantity of manganese-containing by-products. Moreover, the method requires additional treatment steps to remove compounds of heavy metals (manganese) from industrial effluents.

DISCLOSURE OF THE INVENTION

The present invention is based on the problem of developing a method for industrial application that could simplify the production process and exclude the employment of any toxic raw materials and the formation of toxic by-products and would allow one to obtain high-purity products in high yields, which may be used as ozone-safe fire extinguishing agents.

The problem is solved by a method for the preparation of α-substituted ω-hydroperfluoroalkanes of the general formula $H(CF_2CF_2)_nR$ wherein R=H or COOH, and n=1–10 including the oxidation reaction of α, α, ω-trihydroperfluoroalcohols with oxidizing agent in an organic solvent followed by isolation of the desired product, which is characterized by oxidizing α, α, ω-trihydroperfluoroalkanes with oxygen or an oxygen-containing gas in the presence of a homogeneous copper catalyst and an alkaline agent.

As the homogeneous copper catalyst, there are preferably used copper salts of organic or inorganic acids, or copper complexes of o-phenanthroline or bipyridine.

To promote the oxidation of telomeric alcohols sodium hydroxide or potassium hydroxide, or potassium tert.-butoxide is preferably used as the alkaline agent. As the suitable organic solvent, there are preferably used lower aliphatic alcohols, dimethylformamide or sulfolane.

In preparing of ω-hydroperfluorocarboxylic acids, the oxidation of telomeric alcohols is preferably carried out at a temperature of from 30° to 60° C. and a partial pressure of from 0.5 to 1.5 MPa in the presence of an alkaline agent and copper complex of o-phenanthroline or bipyridine as the catalyst in lower aliphatic alcohols. The employment of such conditions allows one to promote the oxidation process and increase in yield and purity of the desired product.

In preparing α, ω-dihydroperfluoroalkanes, the oxidation reaction of α, α, ω-trihydroperfluoroalcohols is preferably carried out at a temperature of from 10° to 40° C. and a partial pressure of from 0.2 to 0.3 MPa in the presence of copper salt soluble in a polar organic solvent and potassium hydroxide in dimethylformamide or sulfolane. The employment of the conditions above allows one to promote the reaction process and increase the yield and the purity of the desired product.

The method of the present invention makes it possible to simplify the production process of α-substituted ω-hydroperfluoroalkanes and exclude the employment of any toxic starting compounds and the formation of toxic by-products. The method of the present invention is suitable for industrial realization, and it allows one to prepare the desired products of high purity and in high yields, which may be used as the ozone-safe fire extinguishing agent.

THE PREFERRED EMBODIMENT OF THE INVENTION

A method for the preparation of α-substituted ω-hydroperfluoroalkanes is carried out as follows.

Into a chemical reactor equipped with an agitator and a heater, there is charged a telomeric alcohol dissolved in an organic solvent. As the solvent, there are preferably used lower aliphatic alcohols, dimethylformamide or sulfolane. Such solvents are oxidation-resistant and show an excellent dissolving power with regard to the catalysts, the starting materials and the reaction products. Subsequently, a solution of a homogeneous copper catalyst is charged into the reactor. A solution of the homogeneous copper catalyst may include copper salts of an organic or inorganic acid, or copper complexes of o-phenanthroline or bipyridine.

On dissolving the catalyst completely, an alkaline agent such as sodium or potassium hydroxide in the form of granules or fine powder, or potassium tert.-butoxide as powder is added to the reaction mixture.

Once the raw materials have been charged, the thermostatic control and the stirrer are brought into action, and the pressurized oxygen or air is admitted into the reactor. The reaction may proceed at room temperature. In preparing ω-hydroperfluorocarboxylic acids as the desired products, in order to increase their yields and promote the oxidation of the raw materials, the reaction is preferably carried out at a temperature of from 30° to 60° C. and a partial pressure of from 0.5 to 1.5 MPa in the presence of an alkaline agent and Cu complex of o-phenanthroline or bipyridine in lower aliphatic alcohols.

In preparing α, ω-dihydroperfluoroalkanes, the reaction process is preferably carried out at a temperature of from 10° to 40° C. and a partial pressure of from 0.1 to 0.3 MPa in the presence of a copper salt in a polar organic solvent, and potassium hydroxide preferably in dimethylformamide or sulfolane.

The desired product is isolated from the reaction mixture by distillation, the residue is washed with water and the aqueous phase is separated. As a result, there is obtained the desired product having purity more than 98%.

The yield of the desired product is of about 94% of the theoretical.

For a better understanding of the present invention, the illustrative examples of a method for the preparation of α-substituted ω-dihydroperfluoroalkanes and their characterization are given below.

EXAMPLE 1

Into a steel-made reactor equipped with an agitator and a jacket, solution of $CuCl_2$ ($5 \cdot 10^{-3}$ mol/l) and o-phenanthroline ($1 \cdot 10^{-2}$ mol/l) in 60 ml of isobutyl alcohol was charged. Thereafter, 59.4 g (0.45 mol) of α, α, ω-trihydroperfluoropropanol (telomeric alcohol, n=1) and 15 g (0.375 mol) of granular sodium hydroxide were added to the reaction mixture. While maintaining the reaction mixture at 45° C. under stirring, oxygen was introduced to the reactor at pressure of 0.5 MPa for 6.5 hours. Subsequently, isobutanol and the unreacted fluorinated alcohol were removed from the reaction mixture by evaporation in vacuum under reflux at 150° C. The content of telomeric alcohol in the overhead product was of 29.4 g.

To the solid residue (40.5 g) 150 ml of concentrated solution of sulfuric acid were added, and the resulting mixture was heated to temperature of 170° C. followed by simultaneous evaporation of the desired product in vacuum to about 150 mm Hg. As a result, there was obtained 24.5 g of ω-hydroperfluoropropionic acid. The conversion of telomeric alcohol (n=1) was of 50.5%, the yield of the title acid based on the alcohol converted was of 73,8%.

Characterization of $HCF_2CF_2COOH$: b.p.135°–137° C., $n_D^{20}=1.3221$, $d_4^{20}=1.5940$, neutralization equivalent: found 147, calculated 146.

Literature source data: b.p.132° C./700 mm Hg, $d_4^{20}=1.563$.

EXAMPLE 2

The procedure of Example 1 was repeated except that 74.0 g of α, α, ω-trihydroperfluoropropanol (telomeric alcohol, n=1), solution containing $CuCl_2$ ($2.5 \cdot 10^{-3}$ mol/l) and o-phenanthroline ($2.5 \cdot 10^{-3}$ mol/l) in 50 ml of isobutanol, and 2.4 g of granular sodium hydroxide were used for the reaction mixture. The oxidation reaction was carried out at temperature of 45° C. and pressure of 1.0 MPa for 4 hours. As a result, 18.5 g of ω-hydroperfluoropropionic acid was obtained. The conversion of telomeric alcohol was of 35.0%, the yield of the title acid in terms of the amount of the converted alcohol was of 65,0%.

EXAMPLE 3

The procedure of Example 1 was repeated except that 180 ml of isobutanol solution containing 148.0 g (1.12 mol) of telomeric alcohol (n=1), $CuCl_2$ ($5 \cdot 10^{-3}$ mol/l) and o-phenanthroline ($1 \cdot 10^{-2}$ mol/l) were used. The process was carried out in the presence of 35.0 g of sodium hydroxide at 50° C. for 4 hours at pressure of 1.0 MPa.

As a result, there was obtained 70.0 g of ω-hydroperfluoro-propionic acid. The conversion of telomeric alcohol was of 55.0%, the yield of the title acid based on the alcohol converted was of 75,0%.

EXAMPLE 4

The procedure of Example 1 was repeated except that 66.2 g (0.285 mol) α, α, ω-trihydroperfluoropentanol were used as the telomeric alcohol (n=2), and a solution containing $CuCl_2$ ($5 \cdot 10^{-3}$ mol/l) and o-phenanthroline ($5 \cdot 10^{-3}$ mol/l) in 60 ml of isobutanol and 10 g (0.25 mol) of sodium hydroxide were added thereto. The oxidation reaction was carried out at temperature of 45° C. and pressure of 0.5 MPa for 3.5 hours.

Thereafter, the solvent and the unreacted telomeric alcohol were removed from the reaction mixture by evaporation in vacuum under reflux at 160° C. The telomeric alcohol content in the overhead product was of 18.2 g. 45.3 g of the residue was decomposed with concentrated sulfuric acid (120 ml) at 180° C. followed by simultaneous removal of the end product from the reaction mixture by evaporation in vacuum to 60 mm Hg. As a result, 34.8 g of ω-hydroperfluoropentanoic acid was obtained. The conversion of telomeric alcohol was of 72.5%, the yield of the title acid in terms of the converted alcohol was of 68,4%.

Characterization of $H(CF_2CF_2)_2COOH$: b.p.165°–167° C., $n_D^{20}=1.3172$, $d_4^{20}=1.7167$, neutralization equivalent: found 249, calculated 246.

Literature sources: b.p.160°–165° C., $n_D^{20}=1.3190$, $d_4^{20}=1.710$.

EXAMPLE 5

The procedure of Example 1 was repeated except that α, α, ω-trihydroperfluoroheptanol (n=3) was used as the telomeric alcohol in the amount of 61.5 g (0.185 mol), and a solution containing CuCl ($1 \cdot 10^{-2}$ mol/l) and o-phenanthroline ($1 \cdot 10^{-2}$ mol/l) in 65 ml of tert-butyl alcohol and 6 g of sodium hydroxide (0.15 mol) were added thereto. The oxidation reaction was carried out at the temperature of 45° C. and the oxygen pressure of 1.0 MPa for 1.5 hours.

After completion of the reaction, the solvent and the unreacted telomeric alcohol were removed from the reaction mixture by evaporation in vacuum under heating to 160° C. The telomeric alcohol content in the overhead product was of 5.5 g. 41.5 g of the residue was decomposed with concentrated sulfuric acid (120 ml) at temperature of 185° C. followed by simultaneous evaporation of the desired product in vacuum at pressure of about 80 mm Hg. As a result, there was obtained 35.0 g of ω-hydroperfluoroenanthic acid. The conversion of telomeric alcohol (n=3) was of 91.0%, the yield of the title acid in terms of the converted alcohol was of 73,5%.

Characterization of $H(CF_2CF_2)_3COOH$: b.p.145°–150° C./150 mm Hg, m.p.27.5°–29° C.

Neutralization equivalent: found 335, calculated 346.

Literature source data:b.p. 190°–195° C., m.p.58°–62° C., $n_D^{20}=1.3180$, $d_4^{20}=1.709$.

EXAMPLE 6

The procedure of Example 5 was repeated except that 87.5 g of α, α, ω-trihydroperfluoroheptanol (telomeric alcohol, n=3), a solution containing $CuCl_2$ ($2.5 \cdot 10^{-3}$ mol/l) and o-phenanthroline ($2.5 \cdot 10^{-3}$ mol/l) in 50 ml of isobutyl alcohol, 8.5 g of granular sodium hydroxide were used. The reaction process was carried out at the temperature of 50° C., and the oxygen pressure of 1.0 MPa. The reaction time was of 2.5 hours. As a result, there was obtained 27.8 g of ω-hydroperfluoroenanthic acid. The conversion of telomeric alcohol (n=3) was of 38.9%, the yield of the title acid in terms of the amount of the converted alcohol was of 78,0%.

EXAMPLE 7

The procedure of Example 5 was repeated except that 61.2 g of α, α, ω-trihydroperfluoroheptanol (telomeric alcohol, (n=3), a solution containing $CuCl_2$ ($1 \cdot 10^{-2}$ mol/l) and o-phenanthroline ($2 \cdot 10^{-2}$ mol/l) in 65 ml of isobutanol, and 6.0 g of sodium hydroxide were used. The reaction process was carried out at the temperature of 45° C., and the oxygen pressure of 0.1 MPa for 3.0 hours. As a result, there was obtained 24.0 g of ω-hydroperfluoroenanthic acid. The conversion of telomeric alcohol (n=3) was of 77.3%, the yield of the title acid in terms of the amount of the converted alcohol was of 48,0%.

EXAMPLE 8

The procedure of Example 5 was repeated except that 122.5 g of α, α, ω-trihydroperfluoroheptanol, a solution containing $CuCl_2$ ($2.5 \cdot 10^{-3}$ mol/l) and o-phenanthroline ($2.5 \cdot 10^{-3}$ mol/l) in 60 of isobutanol, and 12.0 g of sodium hydroxide were used.

The reaction process was carried out at the temperature of 50° C., and the oxygen pressure of 1.0 MPa for 4.5 hours. As a result, there was obtained 43.2 g of ω-hydroperfluoroenanthic acid. The conversion of telomeric alcohol (n=3) was of 45.0%, the yield of the title acid in terms of the amount of the converted alcohol was of 75,0%.

EXAMPLE 9

The procedure of Example 5 was repeated except that 61.2 g of α, α, ω-trihydroperfluoroheptanol, a solution containing $CuCl_2$ ($1 \cdot 10^{-2}$ mol/l) and bipyridine ($2 \cdot 10^{-2}$ mol/l) in 65 ml of tert-butyl alcohol and 6.0 g of sodium hydroxide were used.

The reaction process was carried out at 45° C. at the oxygen pressure of the 1.0 MPa for 1.5 hours. As a result, there was obtained 30.4 g of ω-hydroperfluoroenanthic acid. The conversion of telomeric alcohol (n=3) was of 59.0%, the yield of the title acid in terms of the amount of the converted alcohol was of 81,0%.

EXAMPLE 10

The oxidation reaction of α, α, ω-trihydroperfluorononanol (n=4) was carried out in the manner as described in Example 1. A solution containing $CuCl_2$ ($5 \cdot 10^{-3}$ mol/l) and o-phenanthroline ($5 \cdot 10^{-3}$ mol/l) in 60 ml of isobutanol, 75.6 g (0.175 mol) of telomeric alcohol, n=4 and 7.45 g (0.133 mol) of potassium hydroxide were used. The process was carried out at the temperature of 45° C., and the oxygen pressure of 0.5 MPa for 3 hours.

After completion of the reaction, the solvent and the unreacted telomeric alcohol were evaporated in vacuum under reflux at the temperature of about 160° C. The content of telomeric alcohol (n=4) in the overhead product was of 33.6 g. 41.0 g of the residue was decomposed with concentrated sulfuric acid (100 ml) at a temperature of 175°–185° C. followed by evaporation of the desired product in vacuum to about 20–35 mm Hg. As a result, there was obtained 36.2 g of ω-hydroperfluorononylic acid. The conversion of telomeric alcohol (n=4) was of 55.6%, the yield of the title acid in terms of the converted alcohol was of 83,5%.

Characterization of $H(CF_2CF_2)_4COOH$: b.p.138°–141° C./50 mm Hg, m.p.63°–64° C. Neutralization equivalent: found 449, calculated 446.

Literature source data: b.p.220°–230° C., m.p.62°–68° C.

EXAMPLE 11

The procedure of Example 10 was repeated except that 76 g of α, α, ω-trihydroperfluorononanol, a solution containing $CuCl_2$ ($5 \cdot 10^{-3}$ mol/l) and o-phenanthroline ($1 \cdot 10^{-2}$ mol/l) in 50 ml of n-propyl and 6.0 g of sodium hydroxide were used for the reaction mixture.

The reaction temperature was of 30° C., the oxygen pressure of 1.0 MPa. The reaction time was of 4 hours. As a result, there was obtained 38.2 g of ω-hydroperfluorononylic acid. The conversion of telomeric alcohol (n=4) was of 60.0%, the yield of the title acid in terms of the amount of the converted alcohol was of 81.5%.

EXAMPLE 12

The procedure of Example 10 was repeated except that 76 g of α, α, ω-trihydroperfluorononanol, a solution containing $CuCl_2$ ($5 \cdot 10^{-3}$ mol/l) and o-phenanthroline ($1 \cdot 10^{-2}$ mol/l) in 50 isopropyl alcohol and 6.0 g of sodium hydroxide were used.

The reaction was carried out at 30° C. and the oxygen pressure of 1.0 MPa. The reaction time was of 2.5 hours. As a result, there was obtained 44.2 g of ω-hydroperflourononylic acid. The conversion of telomeric alcohol (n=4) was of 67.8%, the yield of the title acid in terms of the amount of the converted alcohol was of 83.0%.

EXAMPLE 13

The procedure of Example 10 was repeated except that 72 g of α, α, ω-trihydroperfluorononanol, a solution containing $CuCl_2$ ($2.5 \cdot 10^{-3}$ mol/l) and o-phenanthroline ($2.5 \cdot 10^{-3}$ mol/ l) in 50 ml of isopropyl alcohol and 6.0 g of sodium hydroxide were used.

The reaction process was carried out at the temperature of 50° C., and the oxygen pressure of 1.0 MPa. The reaction time was of 3.0 hours. As a result, there was obtained of 35.6 g of ω-hydroperfluorononylic acid. The conversion of telomeric alcohol (n=4) was of 61.4%, the yield of the title acid in terms of the amount of the converted alcohol was of 78.0%.

EXAMPLE 14

The procedure of Example 10 was repeated except that 74 g of α, α, ω-trihydroperfluorononanol, 60 ml of isobutanol solution containing $CuCl_2$ ($5 \cdot 10^{-3}$ mol/l) and o-phenanthroline ($1 \cdot 10^{-2}$ mol/l) and 7.0 g of sodium hydroxide were used.

The reaction temperature was of 50° C., the oxygen pressure of 1.0 MPa. The reaction time was of 3 hours. As a result, there was obtained 22 g of ω-hydroperfluorononylic acid. The conversion of telomeric alcohol (n=4) was of 50.5%, the yield of the title acid in terms of the amount of the converted alcohol was of 57.0%.

EXAMPLE 15.

The oxidation reaction of α, α, ω-trihydroperfluoroundecyl alcohol (n=5) was carried out in the same manner as described in Example 1. Solution containing $CuCl_2$ ($5 \cdot 10^{-3}$ mol/l) and o-phenanthroline ($5 \cdot 10^{-3}$ mol/l) in 60 ml of isobutanol, 84.8 g (0.16 mol) of telomeric alcohol (n=5) and 6.0 g (0.15 mol) of sodium hydroxide were used.

The reaction process was carried out at the temperature of 45° C. and the oxygen pressure of 0.5 MPa for 3.5 hours.

Thereafter, the solvent and the unreacted telomeric alcohol were removed from the reaction mixture by evaporation in vacuum at temperature of 180° C. The content of telomeric alcohol (n=5) in the overhead product was of 27.8 g 56.0 g of the residue was decomposed with concentrated sulfuric acid (100 ml) at temperature of 195° C. followed by simultaneous evaporation of the desired product in vacuum to about 30 mm Hg. As a result, 46.2 g of ω-hydroperfluoroundecylic acid. The conversion of telomeric alcohol (n=5) was of 67.2%, the yield of the title acid in terms of the converted alcohol was of 79.0%.

Characterization of $H(CF_2CF_2)_5COOH$: m.p.104° C.

Neutralization equivalent: found 531, calculated 546.

Literature source data: m.p.100°–101° C.

EXAMPLE 16

Into a 2 l stainless steel-made reactor, there were charged 0.75 l of a solution containing 0.85 g ($2.5 \cdot 10^{-3}$ mol/l) of $CuCl_2 \cdot 2H_2O$ and 1.98 g ($5 \cdot 10^{-3}$ mol/l) of o-phenanthroline in n-butyl alcohol (overall volume of solution 1270 ml) followed by addition of 760 g of admixture of telomeric alcohols of the general formula $H(CF_2CF_2)_nCH_2OH$ including 5% by weight of (n=5), 85% by weight of (n=6) and 10% by weight of (n=7), and 44 g (1.1 mol) of granular sodium hydroxide thereto. Subsequently, the agitator was brought into action, and to the reactor pressurized with oxygen at 5 MPa and the initial temperature of the reaction mixture of 14° C. The temperature inside of the reactor begun to rise gradually due to the exothermic heat, and 45 min later it reached 63° C. Then, the reaction temperature begun to decrease. The oxygen pressure inside of the reactor was adjusted at 4.5 and 5.0 MPa over 45 min. after the commencement of the reaction, whereupon the oxygen supply was cut off. Finally, the reaction mixture was stirred for additional 10 min., with oxygen pressure and temperature of the inside of the reactor being of 4.6 MPa, and 53° C., respectively. As a result, there was obtained 1393 g of the reaction mixture.

Then, the solvent and the unreacted telomeric alcohol were removed from the reaction mixture. The residue was decomposed with concentrated sulfuric acid at temperature of 195° C. followed by simultaneous removal of the desired product by evaporation in vacuum to 30 mm Hg. As a result, there was obtained 251 of mixture of ω-hydroperfluoroalcanoic acids having neutralization equivalent of 578. The conversion of telomeric alcohols was of 46.2%, the yield of the acids in terms of the converted alcohol was of 70.0%.

EXAMPLE 17

The oxidation reaction of α, α, ω-trihydroperfluoropentanol was carried out similarly to that of Example 1 except that a solution containing $CuCl_2$ ($7.5 \cdot 10^{-3}$ mol/l) and o-phenanthroline ($7.5 \cdot 10^{-3}$ mol/l) in 65 ml of isobutanol, 35 g of telomeric alcohol (n=2) and 6 g of potassium hydroxide were used for the reaction mixture.

The reaction was carried out at the temperature of 15° C. and the and oxygen of 1.0 MPa for 5.0 hours. The conversion of telomeric alcohol was of 50%. The yield of ω-hydroperfluorovaleric acid was 25.6 g. This was 82% in terms of the amount of the converted alcohol.

EXAMPLE 18

The oxidation reaction of 1,1,7-trihydroperfluoroheptanol $H(CF_2CF_2)_3CH_2OH$ was carried in the manner as described in Example 1.

0.095 g ($5 \cdot 10^{-4}$ mol) of $Cu(CH_3COO)_2 \cdot H_2O$ and 0.2 g ($1 \cdot 10^{-3}$ mol) of o-phenanthroline was dissolved in 65 ml of isobutanol. To the resulting solution 35 g of telomeric alcohol (n=3) (61 g, 0.18 mol) and 6 g (0.15 mol) of sodium hydroxide were added. The oxidation reaction was carried out at the temperature of 45° C. and the oxygen pressure of 1.5 MPa for 1 hour. The conversion of telomeric alcohol was of 80%. The yield of ω-hydroperfluorenanthic acid was 40.2 g. This was 79% in terms of the amount of the converted alcohol.

EXAMPLE 19

The oxidation reaction of α, α, ω-trihydroperfluoroheptanol $H(CF_2CF_2)_3CH_2OH$ was carried in the manner similar to that of Example 1. 0.05 g ($5 \cdot 10^{-4}$ mol) of $CuCl_2$ and 0.2 g ($1 \cdot 10^{-4}$ mol) of o-phenanthroline was dissolved in 65 ml of isobutanol. To the resulting solution 35 ml of telomeric alcohol (n=3) (61 g, 0.18 mol) and 6 g of sodium hydroxide (0.15 mol) were added.

The oxidation reaction was carried out at the temperature of 45° C. and the oxygen pressure of 1.5 MPa for 1 hour. The conversion of telomeric alcohol was of 78%. The yield of ω-hydroperfluoroenanthic acid was 40.7 g. This was 82% based on the converted alcohol.

EXAMPLE 20.

Into a glass reactor equipped with a thermostatic control and a magnetic stirrer, there were charged 6 g of α, α, ω-trihydroperfluoropentanol $H(CF_2CF_2)_2CH_2OH$, 6.4 g of sulfolane and $5.1 \cdot 10^{-3}$ g ($3 \cdot 10^{-5}$ mol) of $CuCl_2 \cdot 2H_2O$, and the resulting mixture was stirred. After dissolution of the catalyst, 0.5 g (50 g/l) of granular NaOH was added to the reaction mixture. Then, the reactor was pressurized with oxygen at pressure of 0.1 MPa under stirring while keeping the reaction temperature of 50° C. The reaction was carried out for 2 hours. Then, the resulting product was removed from the reaction mixture by evaporation, washed with water, and the aqueous phase was separated. As a result 2.36 g of α, ω-dyhydroperfluorobutane $H(CF_2CF_2)_2H$, b.p.45° C. The conversion of telomeric alcohol was of 56%. The selectivity of the formation of the desired product was of 80%. The yield of the title product was 44.8% of theoretical.

The thus-obtained α, ω-dihydroperfluorobutane was tested for the ozone-safe fire extinguishing agent according to the procedure below.

A metallic evaporation can that had been heated to a temperature of from 80° to 90° C. was placed into a 10 l container that was then sealed hermetically with a transparent cap. Onto the bottom of the can a given quantity of the fire extinguishing agent was introduced with a syringe through the inlet of the cap. Once the test extinguishing agent had volatilized, a gas mixture was pumped into the cylinder for 5 min. Then, the cap was put away, and a tray with burning spirit was placed into the container. The fire extinction time was recorded immediately from the instant when the flame tip had crossed over the plane of the neck the complete flame suppression. A minimum fire-extinguishing concentration was taken to be gas concentration wherein the flame suppression time was of 1 sec. The results of testing the minimum fire extinguishing concentration of α, ω-dihydroperfluorobutane are shown in Tables 1–2.

TABLE 1

Test for minimum fire-extinguishing concentration of α,ω dihydroperfluorobutane

| Added amount of, α,ω-dihydro- perfluoro- butane,10 l cylinder | | α,ω-dihydroper- fluorobutane content,% by | Extinguishing, |
|---|---|---|---|
| ml | g | volume | time,* sec. |
| 1 | 2 | 3 | 4 |
| 3,0 | 4,5 | 5,2 | 46 |
| 4,0 | 6,0 | 6,9 | 30 |
| 4,5 | 6,8 | 8,0 | <1 |
| 5,0 | 7,6 | 8,6 | instant |
| 6,0 | 9,1 | 10,3 | instant |

*self- quenching time of spirit in a cylinder sealed with a cap - 115 sec.

EXAMPLE 21.

Into a 25 dm³ reactor that had been provided with a steam-water jacket, there were charged 9.5 kg of α, α, ω-trihydroperfluoroheptanol $H(CF_2CF_2)_3CH_2OH$, 11 kg of dimethylformamide, and 18 g ($4 \cdot 10^{-5}$ mol) of $CuCl_2 \cdot 2H_2O$. The resulting mixture was stirred, and 1,5 kg (60 g/l) of NaOH was added thereto. After completion of addition of the starting materials, the reactor was pressurized with oxygen under stirring for 1 hour, while keeping the pressure inside of it at about 0.1 MPa and a temperature of from 30° to 40° C. inside.

As a result, 4.9 kg of α, ω-dihydropperfluorohexane $H(CF_2CF_2)_3H$, b.p.90°–95° C. was distilled of the reaction mixture. The conversion of telomeric alcohol was of 90%, the selectivity of 60%. The yield of the desired product was of 54% of theoretical.

The thus-obtained α, ω-dihydroperfluorohexane was tested for ozone-safe fire-extinguishing properties in the manner as described in Example 20.

The test results were shown in Table 2.

EXAMPLE 22.

The reaction process was carried out in the manner as described in Example 20. 4 g of α, α, ω-trihydroperfluorononanol $H(CF_2CF_2)_4CH_2OH$, 7 g of dimethylformamide and $1.7 \cdot 10^{-3}$ g ($1 \cdot 10^{-5}$ mol) of $CuCl_2 \cdot 2H_2O$ were charged into the reactor. After dissolving the catalyst completely, 0.75 g (75 g/l) of the finely-divided KOH was added to the reaction mixture. The reaction was carried out at the temperature of 30° C. and the oxygen pressure of 0.1 MPa for 2 hours. The desired product was removed from the reaction mixture by distillation.

As a result, 3.3 g of α, ω-dihydroperfluorooctane $H(CF_2CF_2)_4H$ was obtained, b.p. 133°–136° C. The conversion of telomeric alcohol was of 94%, the selectivity of 95%. The yield of the desired product was of 89.3% of theoretical.

The thus-obtained α, ω-dihydroperfluorooctane was tested for ozone-safes fire-extinguishing properties in the manner as described in Example 20.

The test results were shown in Table 2.

TABLE 2

Minimum fire-extinguishing concentration of α,ω-dihydroperfluoroalkanes (fire suppression time <1 sec.)

| Example No. | Fire extinguishing agent | Minimum fire- extinguishing concentration, | |
|---|---|---|---|
| | | g/l | volume % |
| 1 | 2 | 3 | 4 |
| 20 | $H(CF_2CF_2)_2H$ | 0.68 | 8.0 |
| 21 | $H(CF_2CF_2)_3H$ | 0.72 | 5.7 |
| 22 | $H(CF_2CF_2)_4H$ | 0.85 | 5.1 |

EXAMPLE 23

The process was carried out in the same manner as in Example 20. 4.0 g of α, α, ω-trihydroperfluoroundecanol $H(CF_2CF_2)_5CH_2OH$, 7.0 g of dimethylformamide, 8.5 mg ($5 \cdot 10^{-5}$ 0.48 g (48 g/l) of NaOH were charged into the reactor. The oxidation reaction was carried out at the temperature of 60° C. and the oxygen pressure of 0.1 MPa for 17 min. As a result, 1.75 g of α, ω-dihydroperfluorodecane $H(CF_2CF_2)_5H$ was obtained, m.p. 77°–78° C. The conversion of telomeric alcohol was of 98%, the selectivity of 47.5%. The yield of the desired product was of 46.5% of theoretical.

EXAMPLE 24

The reaction process was carried out in the same manner as in Example 20. 4.0 g of α, α, ω-trihydroperfluorotridecanol $H(CF_2CF_2)_6CH_2OH$, 7.0 g of dimethylformamide, $1 \cdot 10^{-3}$ g ($1 \cdot 10^{-5}$ mol) of $CuCl_2$ and KOH (50 g/l) were charged into the reactor. The oxidation reaction was carried out at the temperature of 15° C. and the oxygen pressure of 0.1 MPa for 2.5 hours. As a result, 3.5 g of α, ω-dihydroperfluorododecane $H(CF_2CF_2)_6H$ was obtained. The conversion of telomeric alcohol was of 92%, the selectivity of 95%. The yield of the desired product was of 87.4% of theoretical.

EXAMPLE 25

The reaction process was carried out in the manner as described in Example 20. 1.5 g of α, α, ω-trihydroperfluoropropanol $HCF_2CF_2CH_2OH$, 8.5 g of dimethylformamide, $1.7 \cdot 10^{-3}$ g ($1 \cdot 10^{-5}$ mol) of $CuCl_2 \cdot 2H_2O$ and 70 g/l of KOH were charged into the reactor. The reaction temperature was of 10° C., the oxygen pressure of 0.1 MPa. The reaction time was of 3.5 hours. As a result, 1.15 g of α, ω-dihydroperfluoroethane was obtained. the conversion of telomeric alcohol was of 90%, the selectivity of 85%. The yield of the desired product was of 76.5% of theoretical.

EXAMPLE 26

The reaction process was carried out in the manner as described in Example 20. 2.0 g of α, α, ω-trihydroperfluorohenptanol $H(CF_2CF_2)_3CH_2OH$, 8.0 g of dimethylformamide, $1.7 \cdot 10^{-3}$ g ($1 \cdot 10^{-5}$ mol) of $CuCl_2 \cdot 2H_2O$ and 100 g/l of KOH were charged into the reactor. The reaction temperature was of 30° C., the oxygen pressure of 0.1 MPa. The reaction time was of 0.5 hour. As a result, 1.88 g of α, ω-dihydroperfluorohexane was obtained. The conversion of telomeric alcohol was of 100%, the selectivity of 94%. The yield of the desired product was of 94% of theoretical.

EXAMPLE 27

The reaction process was carried out in the manner as described in Example 20. 4.0 g of α, α, ω-trihydropperfluorononanol $H(CF_2CF_2)_4CH_2OH$, 7.0 g of dimethylformamide, $1 \cdot 10^{-2}$ g ($5 \cdot 10^{-5}$ mol) of $Cu(CH_3COO^-)_2$ and 75 g/l of KOH were charged into the reactor.

The reaction temperature was of 30° C., the oxygen pressure of 0.1 MPa. The reaction time was of 1 hour. As a result, 3.36 g of α, ω-dihydroperfluorooctane was obtained. The conversion of telomeric alcohol was of 93%, the selectivity of 91%. The yield of the desired product was of 84% of theoretical.

EXAMPLE 28

The reaction process was carried out in the same manner as in Example 20. 4.0 g of α, α, ω-trihydroperfluorononanol, 7.0 g of dimethylformamide, $5 \cdot 10^{-5}$ mol of Cu complex of o-phenanthroline and 75 g/l of KOH were charged into the reactor. The reaction temperature was of 30° C., the oxygen pressure of 0.1 MPa. The reaction time was of 1 hour. As a result, 3.36 g of α, ω-dihydroperfluorooctane was obtained. The conversion of telomeric alcohol was of 90%, the selectivity of 93. The yield of the desired product was of 84% of theoretical.

EXAMPLE 29

The reaction process was carried out in the same manner as in Example 20. 4.0 g of α, α, ω-trihydroperfluorononanol, 7.0 g of dimethylformamide, $1.7 \cdot 10^{-3}$ g ($1 \cdot 10^{-5}$ mol) of $CuCl_2 \cdot 2H_2O$ and 75 g/l of KOH were charged into the reactor. The reaction temperature was of 30° C. The reaction mixture was oxidized with air at the partial pressure of 0.3 MPa. The reaction time was of 1 hour. As a result, 3.3 g of α, ω-dihydroperfluorooctane was obtained. The conversion of telomeric alcohol was of 96%, the selectivity of 86%. The yield of the desired product was of 82,5% of theoretical.

EXAMPLE 30

The reaction process was carried out in the same manner as in Example 20. 4.0 g of α, α, ω-trihydroperfluorononanol, 7.0 g of dimethylformamide, $1.7 \cdot 10^{-3}$ g ($1 \cdot 10^{-5}$ mol) of $CuCl_2 \cdot 2H_2O$ and 25 g/l of potassium tert. -butoxide were charged into the reactor. The reaction temperature was of 30° C., the oxygen pressure of 0.05 MPa. The reaction time was of 0.3 hour. As a result, 0.72 g of α, ω-dihydroperfluorooctane was obtained. The conversion of telomeric alcohol was of 20%, the selectivity of 89%. The yield of the desired product was of 18% of theoretical.

EXAMPLE 31

In a manner similar to that of Example 20, 4.0 g of an admixture of telomeric alcohols of the formula: $H(CF_2CF_2)_nCH_2OH$ wherein n=6 −10 (with the telomeric mixture contained 5% by weight of n=6, 25% by weight of n=7, 33% by weight of N=8, 32% by weight of n=9 and 5% by weight of n=10), 7.0 g of dimethylformamide, $1.7 \cdot 10^{-3}$ g ($1 \cdot 10^{-5}$ mol) of $CuCl_2 \cdot 2H_2O$ and 0.4 g (40 g/l) of KOH were charged into the reactor. The reaction temperature was of 45° C., the oxygen pressure of 0.1 MPa. The oxidation time was of 4 hour. As a result, 3.2 g of the mixed dihydroperfluoroalkanes of $H(CF_2CF_2)_nH$ was obtained. The resulting composition contained 4% by weight of n=6, 27% by weight of n=7, 32% by weight of n=8, 32% by weight of n=9 and 5% by weight of n=10. The conversion of telomeric alcohols was of 95%, the selectivity of 90%. The yield of the desired product was of 80% of theoretical.

INDUSTRIAL APPLICABILITY

The α-substituted α, ω-hydroperfluoroalkane prepared by the method of the present invention may be used as ozone-safe fire extinguishing agents, both alone or mixtures thereof. In addition, they may be used as solvents, extracting agents as well as the intermediates in the synthesis of mono- and functional compounds and the like.

We claim:

1. A method for preparing α-substituted ω-dihydroperluoroalkanes of the general formula $H(CF_2CF_2)_nR$ wherein R is H or COOH, and n is an integer of 1 to 10 by oxidizing α, α, ω-trihydroperfluoroalcohols in an organic solvent with subsequent isolation of the desired product, characterized in that the oxidation of said α, α, ω-trihydroperfluoroalcohols is carried out by using an oxygen gas or oxygen-containing gas in the presence of a homogeneous copper catalyst and an alkaline agent.

2. A method according to claim 1, characterized in that the homogeneous copper catalyst is selected from the group consisting of a copper salt of an organic acid, copper complexes of o-phenanthroline and copper complexes of bipyridine.

3. A method to claim 1, characterized in that the alkaline agent is selected from the group consisting of sodium hydroxide, potassium hydroxide, and potassium tert-butoxide.

4. A method according to claim 1, characterized in that the organic solvent is selected from the group consisting of lower aliphatic alcohols, dimethyl formamide and sulfolane.

5. A method according to claim 1, characterized in that in preparing ω-hydroperfluorocarboxylic acids the oxidation of the α, α, ω-trihydroperfluoroalcohols is carried out at a temperature of from 30 ° to 60° C. and at a partial oxygen pressure of from 0.5 to 1.5 MPa in the presence of an alkaline agent and a catalyst selected from the group consisting of copper complexes of o-phenanthroline and bipyridine in lower aliphatic alcohols.

6. A method according to claim 1, characterized in that in preparing α, ω-dihydroperfluoroalkanes the oxidation of the α, α, ω-trihydroperfluoroalcohols is carried out at a temperature of from 10° to 40° C. and a partial oxygen pressure of from 0.1 to 0.3 MPa in the presence of a copper salt soluble in an polar organic solvent and potassium hydroxide in dimethylformamide or sulfolane.

* * * * *

UNITED STATES PATENT AND TRADEMARK OFFICE
CERTIFICATE OF CORRECTION

PATENT NO. : 5,495,034
DATED : February 27, 1996
INVENTOR(S) : Skibida et al.

It is certified that error appears in the above-indentified patent and that said Letters Patent is hereby corrected as shown below:

On title page, item [73], delete the assignee section,

"[73] Assignee: Hoechst Aktiengesellschaft, Germany"

Signed and Sealed this

Fifth Day of November, 1996

Attest:

BRUCE LEHMAN

Attesting Officer

Commissioner of Patents and Trademarks